United States Patent
Galkin

(10) Patent No.: US 7,634,049 B2
(45) Date of Patent: *Dec. 15, 2009

(54) MAMMOGRAPHY SYSTEMS AND METHODS, INCLUDING METHODS UTILIZING BREAST SOUND COMPARISON

(76) Inventor: Benjamin M. Galkin, 35 Ivy La., Cherry Hill, NJ (US) 08002

(*) Notice: Subject to any disclaimer, the term of this patent is extended or adjusted under 35 U.S.C. 154(b) by 3 days.

This patent is subject to a terminal disclaimer.

(21) Appl. No.: 12/043,009

(22) Filed: Mar. 5, 2008

(65) Prior Publication Data

US 2008/0240345 A1 Oct. 2, 2008

Related U.S. Application Data

(63) Continuation-in-part of application No. 11/752,142, filed on May 22, 2007, now Pat. No. 7,512,211, which is a continuation-in-part of application No. 11/279, 280, filed on Apr. 11, 2006, now Pat. No. 7,248,668, and a continuation-in-part of application No. 11/582, 243, filed on Oct. 17, 2006, now Pat. No. 7,251,309, which is a continuation of application No. 11/246,419, filed on Oct. 7, 2005, now Pat. No. 7,142,631, which is a continuation-in-part of application No. 10/748,891, filed on Dec. 30, 2003, now Pat. No. 6,975,701.

(51) Int. Cl.
*A61B 6/04* (2006.01)

(52) U.S. Cl. ........................................................ 378/37
(58) Field of Classification Search .................. 378/37, 378/162–165, 167, 177, 180; 128/915, 920, 128/923; 600/490, 493
See application file for complete search history.

(56) References Cited

U.S. PATENT DOCUMENTS 7,512,211 B2 * 3/2009 Galkin ......................... 378/37

* cited by examiner

*Primary Examiner*—Jurie Yun
(74) *Attorney, Agent, or Firm*—Woodcock Washburn LLP

(57) ABSTRACT

Provided are systems using compression devices for a mammography unit, and methods of using the same. The instant mammography units can comprise at least one x-ray transparent inflatable chamber. When fluid is introduced into the chamber, at least one surface of the chamber expands, and the breast and its vasculature are compressed. Fluid may also be released from the chamber, and as the chamber deflates, blood flow to the breast is restored, producing Korotkoff sounds. Sound data may be obtained with respect to both of a patient's breasts, and the sound data from a patient's first breast may be compared with the data obtained from the contralateral breast. The detected sounds, the comparison data, or both may assist a radiologist in identifying regions of interest on a mammogram, and to enhance a computer-assisted detection (CAD) process and a database of mammography images.

30 Claims, 11 Drawing Sheets

MAMMOGRAPHY SYSTEMS AND METHODS, INCLUDING METHODS UTILIZING BREAST SOUND COMPARISON

CROSS REFERENCE TO RELATED APPLICATIONS

This application is a continuation-in-part of U.S. Ser. No. 11/752,142, filed May 22, 2007 (now U.S. Pat. No. 7,512,211), which is a continuation-in-part of U.S. Ser. No. 11/279,280, filed Apr. 11, 2006 (now U.S. Pat. No. 7,248,668) and a continuation-in-part of U.S. Ser. No. 11/582,243, filed Oct. 17, 2006 (now U.S. Pat. No. 7,251,309), which is a continuation of U.S. Ser. No. 11/246,419, filed Oct. 7, 2005 (now U.S. Pat. No. 7,142,631), which is a continuation-in-part of U.S. Ser. No. 10/748,891, filed Dec. 30, 2003 (now U.S. Pat. No. 6,975,701), each of which are herein incorporated by reference in their entirety.

FIELD OF THE INVENTION

The present inventions relate to the field of radiology and particularly to mammography. More particularly, the present inventions relate to mammography compression systems, and methods of their use.

BACKGROUND OF THE INVENTION

Mammography is the process of obtaining x-ray images of the human breast for diagnosis or surgery. It involves positioning a patient's breast in a desired orientation against a cassette holder (also known as a "bucky") of a mammography unit, compressing the breast with a compression device (e.g., a compression paddle), and then exposing the breast to x-rays to create a latent image of the breast on an image receptor. After exposure, the compression device is released. An example of the image receptor is a film in contact with an intensifying screen contained within a cassette. The cassette is inserted into the cassette holder before every image is taken and removed after every image. The film is removed from the cassette and developed to produce a radiographic image of the breast. Another type of image receptor is a solid state device, and the image is obtained electronically.

A complete mammographic study usually involves at least two x-ray exposures of each breast. One exposure is a craniocaudal view in which the breast is compressed in a superior-inferior direction, i.e., from the direction of the patient's head downward, against a tube-side surface of the cassette holder. The plane of the tube-side surface of the cassette holder is parallel to the floor and the x-ray beam is directed vertically downward. A second exposure is a lateral or oblique view in which the breast is compressed mediolaterally, i.e., from the direction of the patient's midline sidewise, against the tube-side surface of the cassette holder which is angled, along with the axis of the x-ray beam, relative to the floor.

Typically, the compression device is a compression paddle, which includes a rectangular flat plate that is attached to the mammography unit between an x-ray tube assembly and the bucky. The edges of the paddle are usually turned upward away from the bucky to provide a smooth curved surface for patient comfort. The compression paddle is usually made of thin, light-transparent, plastic that absorbs only a small fraction of the incident x-ray beam. The compression paddle is moved either manually or by power drive to apply a compression force to the breast, thereby limiting breast motion and flattening the breast against the cassette holder to a near uniform thickness to improve image quality. U.S. Pat. No. 6,049,583 issued to the present inventor discusses methods and apparatus for measuring compression force in mammography. During compression, parts of the patient's body come into contact with the compression paddle. After x-ray exposure, the compression force is released for patient comfort.

As is well known in the field, to properly position the breast, the patient's chest wall or other regions of the body, depending on the desired view, are brought into tight contact with the rigid surfaces of the cassette holder, its edges, and corners. This procedure has the effect of forcing the patent's anatomy to contour to the shape of the cassette holder, which often causes patient discomfort and pain. Oftentimes, overlapping internal structures are present within the breast tissue that can obscure their delineation in a radiographic image. As a result, it is often necessary to reposition the breast slightly in order to arrive at a diagnosis. This requires repositioning the patient for each view with the attendant discomfort due in part to repeat compressions. U.S. Pat. No. 6,850,590 by the present inventor, incorporated herein by reference, discusses methods of reshaping the breast without repositioning.

It is well known that many women find the procedure for compressing the breast to be uncomfortable and for some, even painful. Methods to provide patient comfort during this procedure involve adding cushioning material to the patient contact surfaces of the compression paddle. Examples are described in U.S. Pat. Nos. 6,577,702 and 6,968,033 issued to Lebovic et al.; and U.S. Pat. No. 6,765,984 issued to Higgins, et al. Also, U.S. Pat. No. 6,975,701 and U.S. Patent Publication No. 2006/0050844 by the present inventor, each of which is incorporated herein by reference, describe cushioning devices for compression paddles. U.S. Pat. No. 5,479,927, issued to Shmulewitz discusses a gel pad attached to the patient-contact surface of the compression paddle.

To properly position the patient's breast in a desired orientation before exposure, a technologist is guided by a light beam originating from the x-ray tube assembly that passes through a collimator and the compression paddle to illuminate the area of the bucky that will be exposed to x-rays, i.e., the imaging area. Sometimes, adding cushioning materials to compression paddles blocks the light and impedes proper positioning of the breast.

Other attempts to resolve problems with the compression paddle have included redesigning the shape of the paddle or its angulation, e.g., U.S. Pat. Nos. 4,962,515; 5,199,056; 5,506,877; 5,706,327; 6,974,255.

Angiogenesis plays an important role in the development of breast carcinoma. The use of contrast and molecular imaging agents to detect and/or treat breast cancer also relies on breast vascularity. Unfortunately, traditional mammography systems that exert static compression force on a breast that is positioned between a bucky and a compression paddle are incompatible with studies relating to blood flow during mammography screening, as the static compression force at least partially interrupts blood flow within the breast.

A recent study concluded that the use of computer-aided detection (CAD) in mammography is associated with reduced accuracy of interpretation of screening mammograms, and furthermore that the increased rate of biopsy with the use of computer-aided detection is not clearly associated with improved detection of invasive breast cancer. Fenton J J et al., *N Engl J Med.* 2007 Apr. 5; 356(14):1399-409.

There remains a great need for devices and methods to compress a patient's breast during mammography that can minimize or eliminate the pain and discomfort experienced by the patient. There also exists a need for devices and methods that can compress a patient's breast but that are not incompatible with studies relating to blood flow during mammography. Improvements to CAD sensitivity and specificity during mammography could reduce incidence of unnecessary biopsies, but such improvements have not yet been developed.

SUMMARY OF THE INVENTION

Provided are mammography units, and methods of using the same, for example, in conjunction with imaging of a patient's breasts. The mammography units can compress a breast without the need for a traditional compression paddle, or can compress the breast using a traditional compression paddle in conjunction with a novel compression device. Specialized devices for use with the instant mammography units can comprise at least one x-ray transparent inflatable chamber for containing a fluid, for example, a pressurized gas. When fluid is introduced into the chamber, at least one surface of the chamber expands. As the chamber expands, breast motion is limited and the breast and its vasculature are compressed. Fluid may also be released from the chamber, and as the chamber deflates, blood flow to the breast is restored, producing Korotkoff sounds that may be detected by a sound detection device. Each breast of a patient may separately be subjected to the foregoing procedure, and data produced from the detected sounds (Korotkoff or otherwise) from one breast may be compared with the data produced from the detected sounds from the second (contralateral) breast. The data resulting from such a comparison may be used to enhance various diagnostic modalities, including, for example, a computer-assisted detection process, a mammogram analysis, an evaluation that utilizes a mammography image database, or another process.

The instant systems include a mammography unit comprising a bucky having an imaging area; a compression device comprising an x-ray transparent inflatable chamber; a manifold operatively associated with the inflatable chamber for introducing a fluid into the inflatable chamber, for permitting release of fluid from the inflatable chamber, or both; and, a sound detector, wherein when fluid is introduced into the inflatable chamber of the compression device, at least one surface of the chamber expands and causes expansion of the compression device against a breast positioned on the bucky, and also causes at least partial occlusion of blood flow to the breast, and wherein when fluid is released from the inflatable chamber of the compression device, blood flow is at least partially restored to the breast and Korotkoff sounds are generated that may be detected by the sound detector.

Methods in accordance with the present invention can comprise securing a compression device comprising an x-ray transparent inflatable chamber over a tube-side surface of a patient's breast positioned on an imaging area of a bucky on a mammography unit; at least partially filling the inflatable chamber of the compression device with a fluid, thereby compressing the breast between the inflatable chamber and an imaging area of a bucky and at least partially occluding blood flow to the breast; transmitting x-rays through the breast and onto the mammogram; releasing at least a portion of the fluid from the inflated at least one chamber, wherein the release of the fluid from the at least one chamber controls the resumption of blood flow to the breast; and, detecting sounds generated by the resumption of blood flow to the breast.

Also provided are methods comprising securing a first compression device comprising an x-ray transparent inflatable chamber over an imaging area of a bucky of a mammography unit, so that when a patient's breast is positioned upon the imaging area, the breast is interposed between the first compression device and a compression surface positioned above a tube-side surface of the breast; at least partially filling the inflatable chamber of the first compression device with a fluid, thereby compressing the breast between the inflatable chamber and the compression surface and at least partially occluding blood flow to the breast; transmitting x-rays through the breast; releasing at least a portion of the fluid from the inflatable chamber, wherein the release of the fluid from the chamber controls the resumption of blood flow to the breast; and, detecting sounds generated by the resumption of blood flow to the breast.

Also disclosed are methods comprising securing a first compression device comprising an x-ray transparent inflatable chamber to a compression paddle of a mammography unit having a bucky with an imaging area; at least partially filling the inflatable chamber of the first compression device with a fluid, thereby compressing a patient's breast that is positioned on the bucky between the inflatable chamber and the imaging area and at least partially occluding blood flow to the breast; transmitting x-rays through the breast; releasing at least a portion of the fluid from the inflatable chamber, wherein the release of the fluid from the chamber controls the resumption of blood flow to the breast; and, detecting sounds generated by the resumption of blood flow to the breast.

Also disclosed are methods comprising using a comparison of data derived from the detection of Korotkoff sounds within a patient's first breast and data derived from the detection of Korotkoff sounds within the patient's contralateral breast to interpret a mammogram.

The present methods also include compressing a breast, whereby the resulting compression occludes at least some blood flow to the breast, at least partially relieving such compression, such that blood flow to the breast is at least partially restored, and, detecting Korotkoff sounds within the breast.

All of the methods provided herein may be performed with respect to both breasts of a patient, preferably via separate but identical repetitions of the disclosed method steps. Each of the methods may also further comprise comparing said detected sounds from said first breast with said detected sounds from said contralateral breast. The detected sounds from the first breast and the contralateral breast of the patient may each be converted to an acceptable data format, such as a frequency domain signal, and the sound data corresponding to the first breast may be compared to the sound data corresponding to the contralateral breast. The comparison may provide a comparision metric, and the resulting metric may be used in connection with a CAD process, a mammogram analysis, a comparison with mammography database records, or any combination thereof.

BRIEF DESCRIPTION OF THE DRAWINGS

The present invention will be better understood, and its numerous objects and advantages will become apparent to those skilled in the art by reference to the following detailed description when taken in conjunction with the following drawings, in which.

DETAILED DESCRIPTION OF ILLUSTRATIVE EMBODIMENTS

Figure 1:
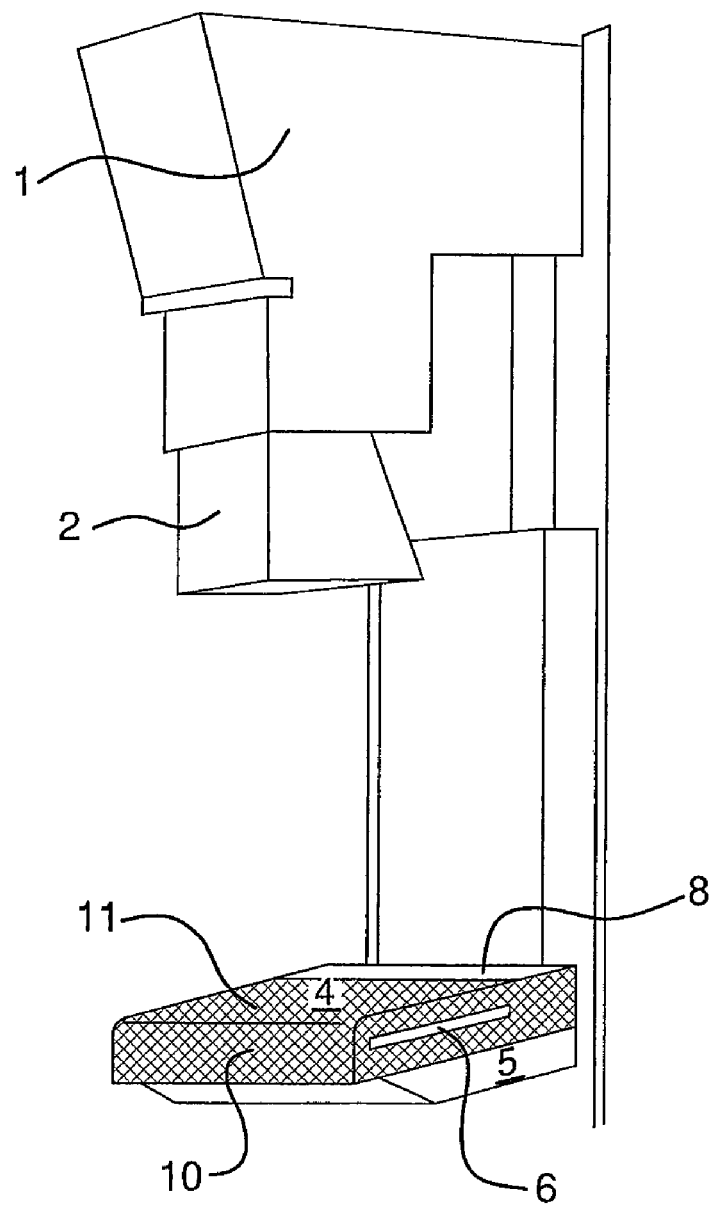
FIG. 1 is a schematic oblique view of a section of a traditional mammography unit.

Provided are mammography systems and methods of using the same, for example, in association with the process of imaging of a patient's breasts.

The instant systems include devices that compress the subject breast (a first breast or a second, contralateral breast) against a bucky without the need for a traditional mammography unit compression paddle. The devices comprise at least one x-ray transparent inflatable chamber for containing a fluid, for example, a pressurized gas. Inflatable chambers can be, for example, medically acceptable balloons. When fluid is introduced into the chamber, at least one surface of the chamber expands. The expansion may be in the direction of the bucky, or may be in the opposite direction, depending on the placement of the device, as described herein.

For example, in one embodiment, the devices secure the breast to the bucky by wrapping over the "tube-side" surface of the breast (so called because it is the surface of the breast that is proximal to the x-ray tube of a mammography unit, whether the x-ray tube is positioned craniocaudally or mediolaterally relative to the breast). The compression devices are preferably adapted for being secured over the tube-side surface of the breast, i.e., include features that permit the compression device to be secured over the tube-side surface of the breast. For example, side flaps, cords, straps, or any other suitable feature can be used to secure the device to and/or around the bucky. Generally, when in position over the breast (and not inflated), the inflatable chamber partially conforms to the shape of the breast. Compressed air, for example, can be introduced, manually or automatically, to inflate the chamber. As the chamber expands, breast motion is limited and the breast is compressed against the surface of the bucky. Inflation of the chamber can at least partially occlude blood flow in the breast.

In another embodiment, the compression devices comprise an x-ray transparent inflatable chamber that is interposed between the breast and the bucky. These compression devices are referred to as being located "bucky-side", as they are positioned at the side of the breast that is proximal to the bucky. Such compression devices are preferably adapted to secure the device on top of the bucky, i.e., include features that permit the compression device to be secured over the tube-side surface of the breast. For example, side flaps, cords, straps, or any other suitable feature can be used to secure the device to and/or around the bucky. Fluid can be introduced to inflate the chamber, and when a paddle or an inflatable chamber device in accordance with the preceding embodiment (i.e., a device that is wrapped over the tube-side surface of the breast) is positioned over the breast, the inflation of the chamber can compress the breast against the paddle or tube-side device. Here, too, inflation of the chamber can at least partially occlude blood flow in the breast.

Traditional mammography units employ a compression paddle, which includes a rectangular flat plate that is attached to the mammography unit between an x-ray tube assembly and the bucky. The compression devices of the instant invention can comprise an x-ray transparent inflatable chamber that is secured to the underside of the paddle, i.e., the side of the flat paddle that is proximal to the bucky. Such compression devices are herein referred to as "paddle-mounted" devices. For example, side flaps, cords, straps, or any other suitable feature can be used to secure the device to and/or around the paddle. Generally, when in position over the breast (and not inflated), the inflatable chamber partially conforms to the shape of the breast. Compressed air, for example, can be introduced, manually or automatically, to inflate the chamber. As the chamber expands, breast motion is limited and the breast is compressed against the surface of the bucky. Inflation of the chamber can at least partially occlude blood flow in the breast.

The inventive system may therefore include a tube-side compression device, a bucky-side compression device, a paddle-mounted compression device, or may comprise a bucky-side device with a paddle-mounted device, or a bucky-side device with a tube-side device.

In each of these embodiments, fluid may be released from the chamber(s) via a valve or some other outlet means, and as the chamber(s) is at least partially deflated, blood flow is restored to the breast, producing Korotkoff sounds that may be detected by a sound detection device.

In 1905, Dr. Nikolai Korotkoff reported that turbulence in blood flow in vivo can produce audible sounds. These sounds are now routinely used to measure blood pressure, typically through use of a stethoscope in conjunction with a blood pressure gauge (sphygmomanometer). However, the detection of Korotkoff sounds has never been used or proposed for use in connection with the mammography process. The instant invention involves the use of Korotkoff sounds during mammography to generate useful data concerning the vascularity of the subject breast. Angiogenesis plays an important role in the development of breast carcinoma, and information concerning the vascularity of a patient's breast can improve the diagnostic process. Furthermore, Korotkoff sounds can provide information about breast vascularity in regions highlighted by computer-assisted detection (CAD) methods. This information could be useful in differentiating between benign and malignant breast conditions prior to biopsy. Currently, it is known that the increased rate of biopsy that has resulted from the use of CAD is not clearly associated with improved detection of invasive breast cancer (Fenton J J et al., 2007), and the introduction of a new data parameter to enhance the CAD process could reduce the incidence of unnecessary biopsies.

In addition, in view of the fact that a standard breast checkup may include the examination of both breasts of a patient, the instant invention may involve the detection of Korotkoff sounds from both a first breast of a patient and the contralateral breast of a patient. Sound data from both breasts may be used to enhance the diagnostic process, for example, by permitting a comparison between the data from a first breast to the data from the contralateral breast; it is frequently the case that a breast condition is present in only one of a patient's breasts, and a difference between the data obtained from a patient's respective breasts can alert a practitioner to the possibility that one of the breasts should be subjected to further examination. The data obtained from a patient's respective breasts may also or alternatively be used, for example, to enhance a computer-assisted detection (CAD) program, to aid in the analysis of a mammogram, in conjunction with the use of a database of mammography images, or any combination thereof.

For example, if an area of interest is identified in a first breast by a CAD program (e.g., by the identification of a location in the image of a breast having a certain pixel value, corresponding to a higher than average optical density), sound data from the area of interest in the first breast may be obtained and compared with sound data from the corresponding anatomical area of interest in the second breast; if the comparison indicates a significant difference between the acoustic properties in the area of interest in the first breast and the acoustic properties in the corresponding area in the second breast, such findings may buttress the findings of the CAD program, and thereby alert the practitioner and/or warrant additional studies. Alternatively, if the difference between the sound data from the first breast and the sound data from the contralateral breast is within a certain range of tolerance, then the practitioner could have reason to suspect that the area of interest as designated by the CAD program is not the site of a malignant growth. It is well known that the blood flow properties, caused, for example, by differences in blood vessel diameter and growth density, are different in cancerous tissue than in normal tissue. Unlike prior methods, the present invention exploits the sounds created by the blood flow properties of a tissue (such as a site of interest) within a breast or the global blood flow properties of a breast, as well as a comparison with corresponding properties in a contralateral breast, in order to obtain valuable additional data parameters regarding the physiological characteristics of a patient's breasts.

The comparison of sound data obtained from a patient's respective breasts can also be used to generate a data metric that can be used to enhance the evaluation of a CAD-generated tissue analysis, of a mammogram, of a set of data obtained from a mammography database, or any combination thereof. As used herein, the "metric" is simply a data parameter that results from the comparison of data obtained through the detection of sounds from a first breast of a patient with data obtained through the detection of sounds from a second, contralateral breast of the patient. The metric may be a sound frequency ratio that can be compared to a ratio that was obtained from a pair of breasts in which a cancerous growth was known to be absent, to a ratio that was obtained from a pair of breasts in one of which breasts a cancerous growth was known to be present, or both. For example, if the metric consists of a ratio, it may be known to the practitioner that ratios that are between 1.5:1 and 1:1.5 represent breasts in which there are not significant tissue differences (which would otherwise indicate tissue properties in one breast that are not present in the other breast). On the other hand, if the ratio is found to be outside of a known range of tolerance, such a finding may be indicative of a clinically significant difference in the blood flow characteristics (and therefore the tissue properties) between a first breast and the contralateral breast. In another embodiment, the metric may be an amplitude ratio, a time ratio, or a combination of any of the preceding.

Thus, in the present invention, the inflatable chamber can effectively function in the manner of a blood pressure cuff, and the sound detector can be used to ascertain Korotkoff sounds, which can in turn be used, alone or in connection with the CAD process, to enhance and improve the process of assessing the condition of the subject breast. For example, the current invention can be used to identify blood flow sounds in a breast at regions of interest as identified by CAD methods, thereby providing an additional parameter to the process of assessing a breast for the presence or absence of cancerous growth. A comparison between the Korotkoff sounds obtained from a first breast and those obtained from a contralateral breast yields additional data that can also be applied to the evaluation of a CAD image, a mammogram, and/or a comparison to database records.

Additionally, because the inflatable chamber can be used to gate blood flow to the breast during the mammography process, unlike traditional devices and methods, the present invention is compatible with contrast and molecular imaging studies that rely on the access of imaging agents to breast vascularity. For example, x-ray absorbing contrast material is systemically administered to a patient via injection. Under this manner of administration, if it is desired to utilize the contrast material by x-ray imaging of the breast, it is difficult to ascertain the precise time at which the contrast material enters the breast in order to capture an x-ray image of the breast at the moment of such entry. Because the instant inflatable chamber can be used to gate blood flow into a compressed breast, i.e., determine the precise time at which blood from the body is permitted to reenter the breast following compression, the present invention permits a clinician to time the capture of an x-ray image of the breast just as blood containing a contrast material resumes its flow into that breast. The x-ray image featuring the contrast material as distributed within the breast can be used to improve the diagnosis of the subject, for example, by aiding in the interpretation of CAD-generated data.

There are also provided mammography units comprising a bucky having an imaging area; a compression device comprising an x-ray transparent inflatable chamber and a manifold operatively associated with the inflatable chamber for introducing a fluid into the inflatable chamber and/or for receiving the fluid from the inflatable chamber; and, a sound detector capable of detecting Korotkoff sounds, wherein when fluid is introduced into the chamber of the compression device, at least one surface of the chamber expands and causes expansion of the compression device against a breast positioned on the bucky and causes at least partial occlusion of blood flow to the breast, and wherein when fluid is released from the inflatable chamber of the compression device, blood flow is at least partially restored to the breast and Korotkoff sounds are generated that may be detected by the sound detector. In one embodiment, a source of compressed air that is in fluid communication with the manifold is provided.

Inflatable chambers increase in volume when pressurized fluid is introduced. A medically acceptable balloon is an example of an inflatable chamber. Chambers used in embodiments of the present invention can be, for example, high pressure balloons. High pressure balloons are used in various applications in the medical industry, such as in angioplasty. See Saab, Applications of High-Pressure Balloons in the Medical Device Industry, http://www.advpoly.com/News-Data/BalloonPaper.pdf. (http://www.devicelink.com/mddi/archive/00/09/003.html)

In some embodiments, the device comprises multiple inflatable chambers. For example, a second inflatable chamber can be used to help distribute the compression force exerted against the breast. The shape of the chambers can vary as needed. In the present disclosure, recitation of "an x-ray transparent inflatable chamber" can mean "at least one x-ray transparent inflatable chamber." More generally, in the present disclosure the singular forms "a," "an," and "the" include the plural reference, and reference to a particular numerical value includes at least that particular value, unless the context clearly indicates otherwise. Thus, for example, a reference to "a sound detector" is a reference to one or more of such sound detectors and equivalents thereof known to those skilled in the art, and so forth. For purposes of the present disclosure, all references to devices or methods in which "a breast" or "the breast" is analyzed are intended to embrace the analysis of one breast of a patient or both breasts of the patient. For example, it is intended that any method that is described with respect to a breast of a patient is applicable to the other breast of a patient, and any method steps recited therein with respect to one breast may be repeated in connection with the second breast of the patient. Furthermore, it is preferred that such method steps are performed separately with respect to each breast; for example, the step of "detecting sounds within the first breast and within the contralateral breast when such breasts are not compressed" means that the detection of sounds within the first breast is performed in an episode that is separate but identical to the detection of sounds within the contralateral breast.

In some embodiments, there is an x-ray transparent cover that substantially surrounds the inflatable chamber. The x-ray transparent cover can be compressible. The x-ray transparent cover can also or alternatively be disposable. For example, in one embodiment, a cuff made of compressible material can have a pocket for holding a high pressure balloon where the cuff wraps around the breast and the bucky. In another embodiment, to avoid direct contact with the patient's skin, a disposable x-ray transparent thin plastic sheet can be used between the tube-side surface of the breast and the inflatable chamber.

Any portion of the instant devices can comprise radiopaque indicia. For example, the indicia can impart information onto the mammogram in an area away from the breast.

Regarding indicia, it may be desirable to provide information including, but not limited to, the physical properties of the compression device, such as density or thickness, the location of the device, the manufacturer of the device, and/or the date of manufacture. In addition, it may be useful for compression devices to have unique serial numbers, that may, for example, aid in tracking re-use of the devices. In accordance with the present invention, information can be provided on the mammogram in an area away from an image of the breast.

Reference herein to "cassette holder" and "bucky" means the device that holds an image receptor for the creation of a mammogram, regardless of whether the image receptor is film-based or digital.

An identifier is radiopaque such that identifying indicia can be either x-ray transparent or radiopaque, and the remaining portion of the identifier would be radiopaque or x-ray transparent, respectively. By reference to the radiopaque nature of an identifier, it is understood that the identifier may not be completely radiopaque, but its radiopacity would be sufficiently different from the radiopacity of the surrounding materials, e.g., x-ray transparent compressible materials or x-ray transparent covers, so as to be recordable, e.g., radiographically, on a mammogram. The identifier can comprise a variety of radiopaque materials, e.g., paper, plastic, or metal. In such an embodiment, identifying indicia would be x-ray transparent. If desired, in another embodiment, identifying indicia can be imprinted with radiopaque ink onto x-ray transparent compressible material or x-ray transparent covers.

As used herein, the "sound detector" is any device that is capable of detecting those sounds that are produced by the flow of blood within tissue, such as a subject breast. For example, any device that functions comparably with a stethoscope may be used. Electronic sound detectors include sensors that may be taped to the outer surface of patient skin at particular locations or that may be affixed proximate to the inflatable chamber of a compression device. When affixed proximate to the inflatable chamber of a compression device, the sound detectors are ideally placed in fluid communication with such inflatable chamber, so that Korotkoff sounds can travel from their locus of origin within the breast to the sound detector via the inflatable chamber, and such configuration works best when the inflatable chamber is at least partially filled with fluid. Preferably, the sound detector is adapted to generate an electrical signal that can be converted to a frequency domain signal that can in turn be digitized for computer storage. More preferably, the sound detector is adapted to permit transfer of the detected sound information to a separate device that can convert the detected sound information to a frequency domain signal that can be digitized for computer storage. Frequency domain signal conversion and digitization are processes that are widely understood by those skilled in the art, and the skilled artisan will readily appreciate how a sound detector may be adapted for use with such processes.

As sound detectors will typically be only partially x-ray transparent (if at all), the sound detectors are ideally a) positioned outside of the x-ray field; b) controlled manually or automatically to enter the x-ray field of the mammography unit at preselected times, i.e., when x-ray images are not being captured; or, c) easily movable from within the x-ray field to outside of the x-ray field.

Preferably, the sound detectors can be activated at any time during the mammography process. For example, sound detectors can be used to detect sounds from within a breast prior to compression by an inflatable chamber, during compression by an inflatable chamber, as compression by an inflatable chamber is being relieved by partial deflation of the inflatable chamber, and/or after compression of the breast has been fully relieved. Episodes of sound detection may be performed at any time in relation to the capture of x-ray images.

Sounds that are ascertained by the sound detector and converted to recordable data can subsequently be compared with libraries of sounds from known cases of cancer, for example, to determine the probability of malignancy. A clinician can also correlate Korotkoff sound data with the information regarding visual mammography features stored in the Digital Database for Screening Mammography ("DDSM"). The DDSM is a publicly available library of features observed on mammograms that can be used as a reference during the diagnostic process. See Heath M et al., "*The Digital Database for Screening Mammography*", in *The Proceedings of the 5th Int'l Workshop on Digital Mammography* (Toronto, Canada, June 2000), Medical Physics Publishing (Madison, Wis.). As used herein, a "mammography database" may include databases of mammography images, whether such images are digitized or analog.

The CAD process as used in connection with mammogram analysis has recently been criticized as being responsible for the generation of false positives and the performance of unnecessary biopsies (Fenton J J et al., 2007). The data acquired through use of the sound detector can be integrated into a CAD algorithm, thereby providing a refinement of the CAD process by introducing an additional data parameter (i.e., Korotkoff sound).

The preceding is also true with respect to a comparison of the sound data that are ascertained from a first breast of a patient with the sound data that are ascertained from the contralateral breast of a patient. The comparison of the sound data from the respective breasts of a patient can be used to generate a metric, for example, a ratio, that can be evaluated in the light of comparable data from subjects in which an abnormal condition was known to be absent, known to be present, or both. In other words, comparison of a such a metric with information from a database can provide the diagnostician with information pertaining to the condition of one or both of the patient's breasts.

Methods in accordance with the present invention can comprise securing a compression device comprising an x-ray transparent inflatable chamber over a tube-side surface of a patient's breast positioned on an imaging area of a bucky on a mammography unit; at least partially filling the inflatable chamber of the compression device with a fluid, thereby compressing the breast between the inflatable chamber and the imaging area and at least partially occluding blood flow to the breast; transmitting x-rays through the breast; releasing at least a portion of the fluid from the inflatable chamber, wherein the release of the fluid from the chamber controls the resumption of blood flow to the breast; and, detecting sounds generated by the resumption of blood flow to the breast. The instant methods may be performed with respect to both breasts of a patient, preferably via separate but identical repetitions of the disclosed method steps. The methods may also further comprise comparing said detected sounds from said first breast with said detected sounds from said contralateral breast. The detected sounds from the first breast and the contralateral breast of the patient may each be converted to an acceptable data format, such as a frequency domain signal, and the sound data corresponding to the first breast may be compared to the sound data corresponding to the contralateral breast. The comparison may provide a comparison metric, and the resulting metric may be used in connection with a CAD process, a mammogram analysis, a comparison with mammography database records, or any combination thereof.

Also provided are methods comprising securing a first compression device comprising an x-ray transparent inflatable chamber over an imaging area of a bucky, so that when a patient's breast is positioned upon the imaging area, the breast is interposed between the first compression device and a compression surface positioned above a tube-side surface of the breast; at least partially filling the inflatable chamber of the first compression device with a fluid, thereby compressing the breast between the inflatable chamber and the compression surface and at least partially occluding blood flow to the breast; transmitting x-rays through the breast; releasing at least a portion of the fluid from the inflatable chamber, wherein the release of the fluid from the chamber controls the resumption of blood flow to the breast; and, detecting sounds generated by the resumption of blood flow to the breast. The instant methods may be performed with respect to both breasts of a patient, preferably via separate but identical repetitions of the disclosed method steps. The methods may also further comprise comparing said detected sounds from said first breast with said detected sounds from said contralateral breast. The detected sounds from the first breast and the contralateral breast of the patient may each be converted to an acceptable data format, such as a frequency domain signal, and the sound data corresponding to the first breast may be compared to the sound data corresponding to the contralateral breast. The comparison may provide a comparison metric, and the resulting metric may be used in connection with a CAD process, a mammogram analysis, a comparison with mammography database records, or any combination thereof.

The compression surface can be a traditional paddle or can be a tube-side compression device as described previously. When the compression surface is a paddle, a paddle-mounted compression device comprising an x-ray transparent inflatable chamber can be secured thereto; the paddle-mounted compression device can also be at least partially filled with a fluid and used to compress the breast between itself and the bucky-side compression device.

The inventive methods can include the use of both a compression device that is secured over the tube-side surface of a breast and a compression device that is secured to the mammography unit between the breast and the bucky, or both a compression device that is paddle-mounted and a compression device that is secured to the mammography unit between the breast and the bucky, inflating one or more chambers of either or both of the compression devices; compressing a breast; transmitting x-rays through the breast, releasing at least a portion of the fluid from the inflated chambers of the compression devices, and detecting sounds generated by the resumption of blood flow into the breast.

Also disclosed are methods comprising securing a first compression device comprising an x-ray transparent inflatable chamber to a compression paddle of a mammography unit having a bucky with an imaging area; at least partially filling the inflatable chamber of the first compression device with a fluid, thereby compressing a patient's breast that is positioned on the bucky between the inflatable chamber and the imaging area, and at least partially occluding blood flow to the breast; transmitting x-rays through the breast; releasing at least a portion of the fluid from the inflatable chamber, wherein the release of the fluid from the chamber controls the resumption of blood flow to the breast; and, detecting sounds generated by the resumption of blood flow to the breast. The instant methods may be performed with respect to both breasts of a patient, preferably via separate but identical repetitions of the disclosed method steps. The methods may also further comprise comparing said detected sounds from said first breast with said detected sounds from said contralateral breast. The detected sounds from the first breast and the contralateral breast of the patient may each be converted to an acceptable data format, such as a frequency domain signal, and the sound data corresponding to the first breast may be compared to the sound data corresponding to the contralateral breast. The comparison may provide a comparison metric, and the resulting metric may be used in connection with a CAD process, a mammogram analysis, a comparison with mammography database records, or any combination thereof.

The instant methods can further comprise using a source of compressed air to inflate the chamber of the compression device.

With respect to the present methods, the detection of sounds may be performed prior to compression of a patient's breast, during compression of a patient's breast, or following compression of a patient's breast. The detection of sounds within the breast may also be conducted at any stage of compression of the breast, i.e., when the breast is only partially compressed, or when the breast of fully compressed. When the sound detection step occurs at a specific stage during the instant methods with respect to a first breast, a sound detection step should also be performed at the same stage in the contralateral breast so that appropriate data comparisons may be made. When the methods involve the use of a compression device having an inflatable chamber, the detection of sounds within the breast may occur prior to at least partially filling the chamber of the compression device, when the chamber of the compression device has been at least partially filled, when the fluid introduced into the chamber of the compression device has been at least partially released from the chamber, when the fluid has been released from the chamber to the extent necessary to allow blood flow to the breast to be at least partially restored, or when the fluid has been released from the chamber to the extent necessary to allow blood flow to the breast to be substantially completely restored. One or more x-ray images of the breast may be acquired at any stage during the performance of the instant methods in relation to the detection of sound or the compression of the patient's breast.

The detection of sounds generated by the resumption of blood flow to the breast may be conducted locally (i.e., at a portion or portions of the breast), or may be conducted over the entire breast ("globally"). If sound is detected locally, the portion(s) of the breast at which sound is detected may be a site of interest. A site of interest may be determined through reference to an image of the breast that was acquired prior to the sound-detection stage. For example, sound may be detected locally at a site of interest as identified through CAD methods. Once identified, the sound data retrieved from a site of interest within one breast may be compared with sound data that is retrieved from the corresponding anatomical location on the contralateral breast. The comparison can yield information regarding whether the site of interest is physiologically distinguishable from comparable tissue that is otherwise believed to be normal. Such findings may buttress the findings of the CAD program, and thereby alert the practitioner and/or warrant additional studies; alternatively, if the difference between the sound data from the first breast and the sound data from the contralateral breast is within a certain range of tolerance, then the practitioner could have reason to suspect that the area of interest as designated by the CAD program is not the site of a malignant growth.

In another embodiment, the methods can additionally comprise converting the detected sounds to an acceptable data format, such as a frequency domain signal. The converted sounds can be digitized for computer storage. The converted sounds can also be compared to sounds detected from other tissue samples. The tissue samples can be from a breast, including from a contralateral breast of the same patient, and the breast can be one in which cancerous growth is known to be absent, or can be one in which cancerous growth is known to be present.

The inventive methods can further comprise introducing a detectible agent into the subject to which the breast belongs, or directly into the breast. The detectible agent may be a molecular agent, or a contrast agent, or both a molecular agent and a contrast agent may be introduced into the subject/breast. In most instances, when a detectible agent is introduced into one breast of a patient, normal blood flow will cause the detectible agent to enter the contralateral breast; however, if sufficiently small quantities of a detectible agent are used, it may be necessary to introduce the detectible agent into both of the patient's breasts. In another embodiment, the methods can comprise introducing a detectible agent into the subject or subject's breast, releasing at least a portion of the fluid from the inflated chambers of the compression devices, and imaging the breast. Exemplary molecular agents include radioactive agents. The contrast material is preferably an x-ray absorbing substance, such as an iodide compound, but may be another material. Thus the inventive methods can include introducing an iodide compound into the subject/breast, releasing at least a portion of the fluid from the inflated chambers of the compression devices, and imaging the breast, i.e., just as the iodide compound enters the breast via the resumption of blood flow. Unlike existing mammography devices and methods, the present invention is compatible both with traditional mammography procedures (e.g., x-ray imaging) and with procedures that require the at least partial resumption of blood flow within the breast, such as Korotkoff sound detection (as herein described), and techniques that involve the deployment of detectible agents such as molecular or contrast agents within the breast vasculature.

Also provided are methods comprising using data derived from the detection of Korotkoff sounds within a breast to interpret a mammogram. In accordance with the present invention, data that are derived from the detection of Korotkoff sounds within a patient's first breast are compared with data derived from the detection of Korotkoff sounds within the patient's contralateral breast in order to interpret a mammogram. In some instances, the data may be used to designate one or more regions of interest on a mammogram. The sound data may be used by a radiologist to interpret a mammogram (including to designate one or more regions of interest on a mammogram), or may be used during a computer-assisted detection (CAD) process in order to interpret a mammogram such as by flagging regions of interest for review by a radiologist, or both. In either of the latter two instances, the CAD process may make use of an algorithm that is specially adapted for integrating sound data into the interpretation and/or flagging process. In a typical examination, a radiologist will compare the image obtained from one breast to the image obtained from the contralateral breast of the patient to identify regions of interest. Likewise, the sound pattern from a breast having a malignancy can be expected to be distinguishable from the sound pattern from contralateral breast without a malignant growth.

Also disclosed are methods comprising compressing a breast, whereby the resulting compression occludes at least some blood flow the breast; at least partially relieving the compression, such that blood flow to the breast is at least partially restored, and detecting Korotkoff sounds within the breast. As previously indicated, the instant methods may be performed with respect to both breasts of a patient, preferably via separate but identical repetitions of the disclosed method steps. The sound detection step may occur at any stage during the instant methods, but it is preferred that at least one instance of sound detection be performed following the compression stage when blood flow to the breast has at least partially resumed. In addition, when the sound detection step occurs at a specific stage during the instant methods with respect to a first breast, a sound detection step should also be performed at the same stage in the contralateral breast so that appropriate data comparisons may be made. Once sounds have been detected the sound data may be converted to a frequency domain signal or other acceptable data format, such conversion being readily understood by those skilled in the art. In accordance with the present invention, sound data that is obtained from the first of a patient's breasts may be compared with the sound data that is obtained from the patient's contralateral breast. The data comparison may be used to yield a comparison metric, which may, for example, take the form of a ratio. The metric may be used during the analysis of at least one of a computer-assisted detection process, a mammogram, or a database of mammography images. The sound data may be used to designate regions of interest within a breast, for example, in any manner as described previously, such as by a radiologist, or during the process of computer-assisted detection (CAD) or both. The instant methods may additionally comprise transmitting x-rays through the breast in order to obtain a mammogram. One or more x-ray images of the breast may be acquired at any stage during the performance of the instant methods in relation to the detection of sound or the compression of the patient's breast.

Figure 2:
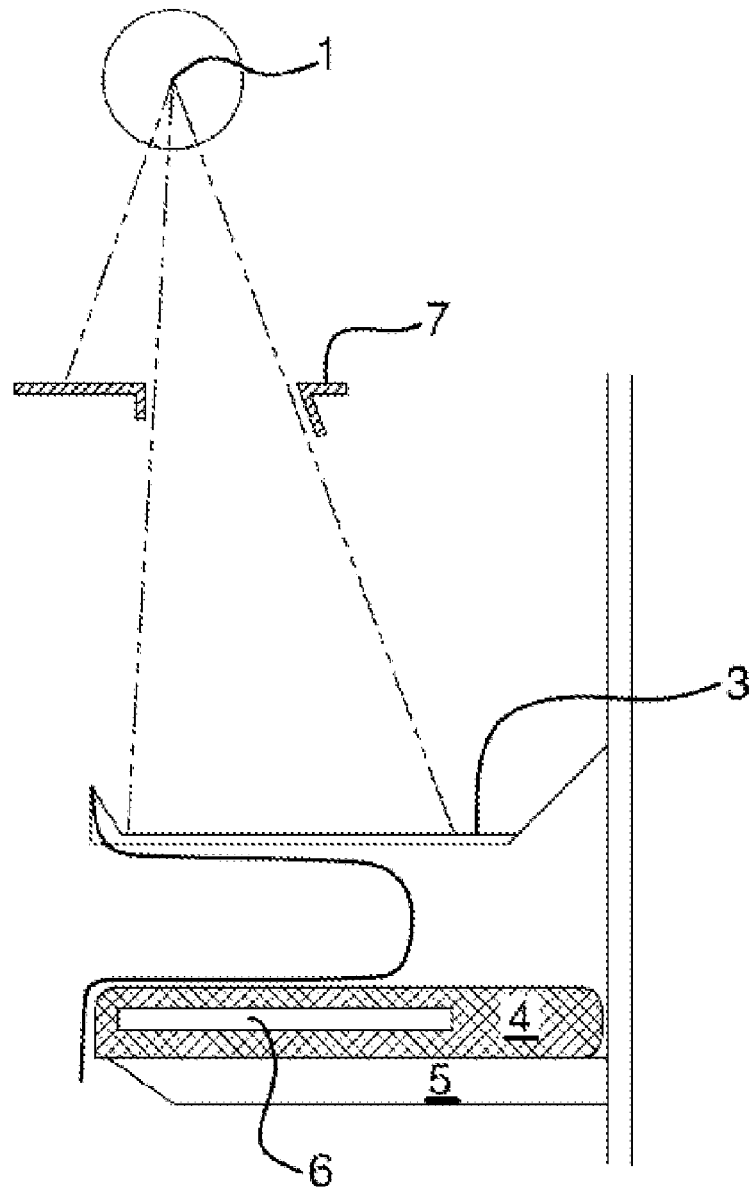
FIG. 2 is a schematic lateral view of FIG. 1 depicting a breast compressed with a compression surface.

Referring now to the drawings wherein reference numerals refer to like elements, FIGS. 1 and 2 depict two views of a mammography unit in accordance with an embodiment of the present invention having an x-ray tube 1 that produces an x-ray beam (not numbered) connected to a cone 2 that houses a collimator 7. The collimator 7 restricts the size and shape of the x-ray beam in any plane perpendicular to the axis of the x-ray beam. The x-ray beam also passes through a compression surface 3, which may be a paddle or a compression device according to the present invention. A cassette holder 4, comprises a tube-side surface containing an imaging area 11 and a solid area 8; an outer surface 10 that is in close proximity or in contact with a patient's chest wall during examination; and a cassette tunnel opening 6. Generally, in a film-based cassette holder, a cassette tunnel located below the imaging area houses an antiscatter grid and a cassette. The cassette holder 4 is held in place by a support member 5 and slidably engages with a support column (not numbered). The x-ray beam passes through imaging area 11 to expose a film in the cassette. In a digital unit, the cassette tunnel openings are not present. X-ray beams used in conjunction with a digital bucky are received electronically. The solid area 8 is typically not transparent to x-ray beams and secures the cassette holder or bucky to the support column. A patient's breast (not numbered) is positioned on the imaging area 11 of the tube-side surface of the cassette holder 4 and is compressed by the compression surface 3.

Figure 3:
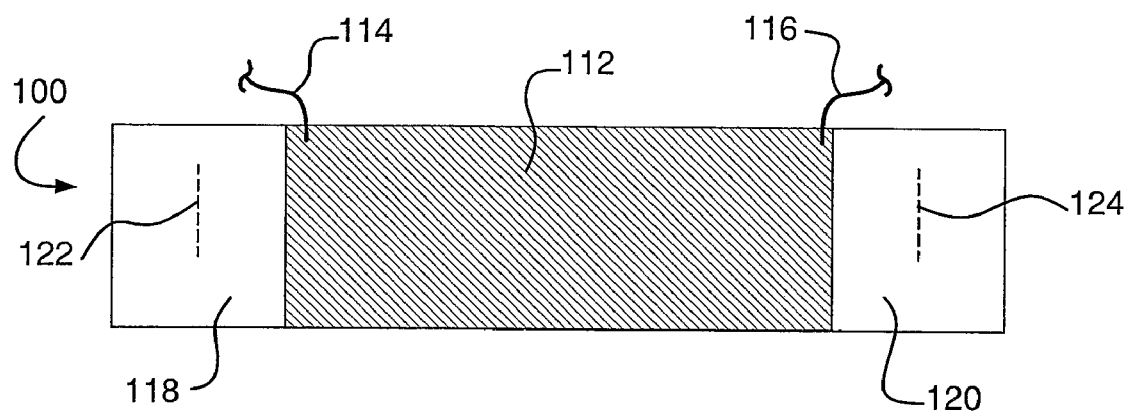
FIG. 3 is a schematic top view of an embodiment of the tube-side compression devices of the present invention.
Figure 4:
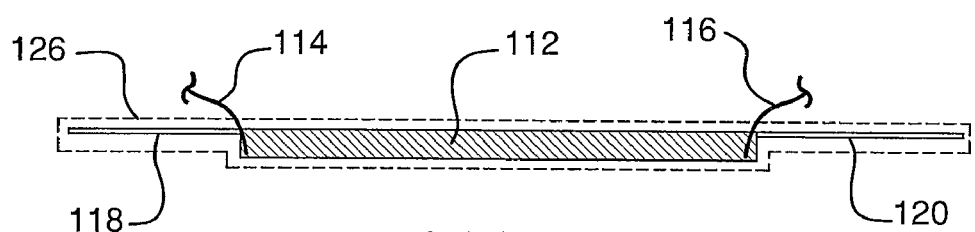
FIG. 4 is a schematic side view of an embodiment of the tube-side compression devices of the present invention.

FIG. 3 is a schematic top view of an embodiment of the present invention. FIG. 4 is a schematic side-view of an embodiment of the present invention. An x-ray transparent inflatable chamber 112 has at least one manifold 114 that is operatively associated with the chamber 112, which can introduce compressed gas, for example, into the chamber and/or receive compressed gas to vent it from the chamber. A source of fluid, for example, compressed air, enters the chamber 112 of the device 100 through a manifold 114. An optional second manifold 116 can be operatively with the chamber for venting or fluid inlet purposes. The device 100 may be used in securing a patient's breast to a bucky by wrapping over the breast. The device 100 can alternatively be mounted onto a paddle, for example, by wrapping over the underside of the paddle. In an embodiment, one or more flaps, 118 and 120, made of, for example, adhesive or elastic, attach to one or more ends of the chamber. When device 100 is used in securing a patient's breast to a bucky by wrapping over the breast, the flaps optionally have one or more openings 122, 124 to permit a film cassette to pass through them into the cassette holder.

In some embodiments, an x-ray transparent cover 126 substantially surrounds the inflatable chamber. In some instances, it may be desirable that the x-ray transparent cover is compressible. In other instances, the x-ray transparent cover is disposable. A combination of compressible and disposable covers can also be used. For example, in one embodiment, a cuff made of compressible material can have a pocket for holding a high pressure balloon where the cuff wraps around and/or releasably adheres to the breast and the bucky.

In one embodiment, the inflatable chamber has multiple chambers. In one example, a chamber is nested within the cavity of another chamber. Another example is a combination of chambers next to each other. The use of multiple chambers can be used to help distribute the compression force exerted against the breast. The shape of the chambers can vary as needed too.

In evaluating equivocal areas of a mammogram it is sometimes desirable to provide a greater degree of compression in a localized area of a breast than can be achieved by uniform compression. This procedure, called spot compression, can be accomplished with the present invention by configuring at least one surface of the chamber with an area that expands to a greater degree than the surrounding surface, and positioning this area over the region of interest. Alternatively, an x-ray transparent semi-rigid plastic disc can be placed on the breast over the area of interest before overlaying the breast with the compression device. As air is introduced into the chamber, the disc is pushed against the breast to exert additional compression force in the localized area. The discs can vary in size as needed. Identical episodes of spot compression may be separately performed with respect to each of a patient's breasts. Preferably, if a certain variation on compression is performed with respect to a first of a patient's breasts, then the same type of compression should be performed for purposes of the analysis of the second of the patient's breasts.

Figure 5:
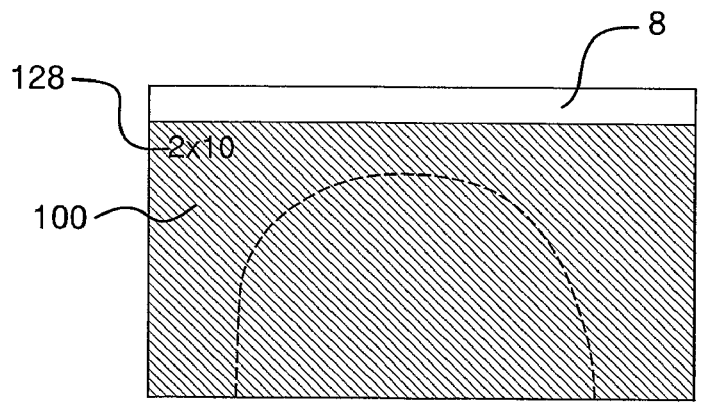
FIG. 5 is a top view of an embodiment of the tube-side compression devices of the present invention.

Any portion of the devices can comprise radiopaque indicia. FIG. 5 is a top-view of a device 100 that wraps over the tube-side area of a breast and contacts the surface of the bucky. Optionally, indicia 128 is contained on a surface of the device 100. Preferably, the indicia imparts information onto the mammogram in an area away from the breast.

Figures 6A, 6B, 6C:
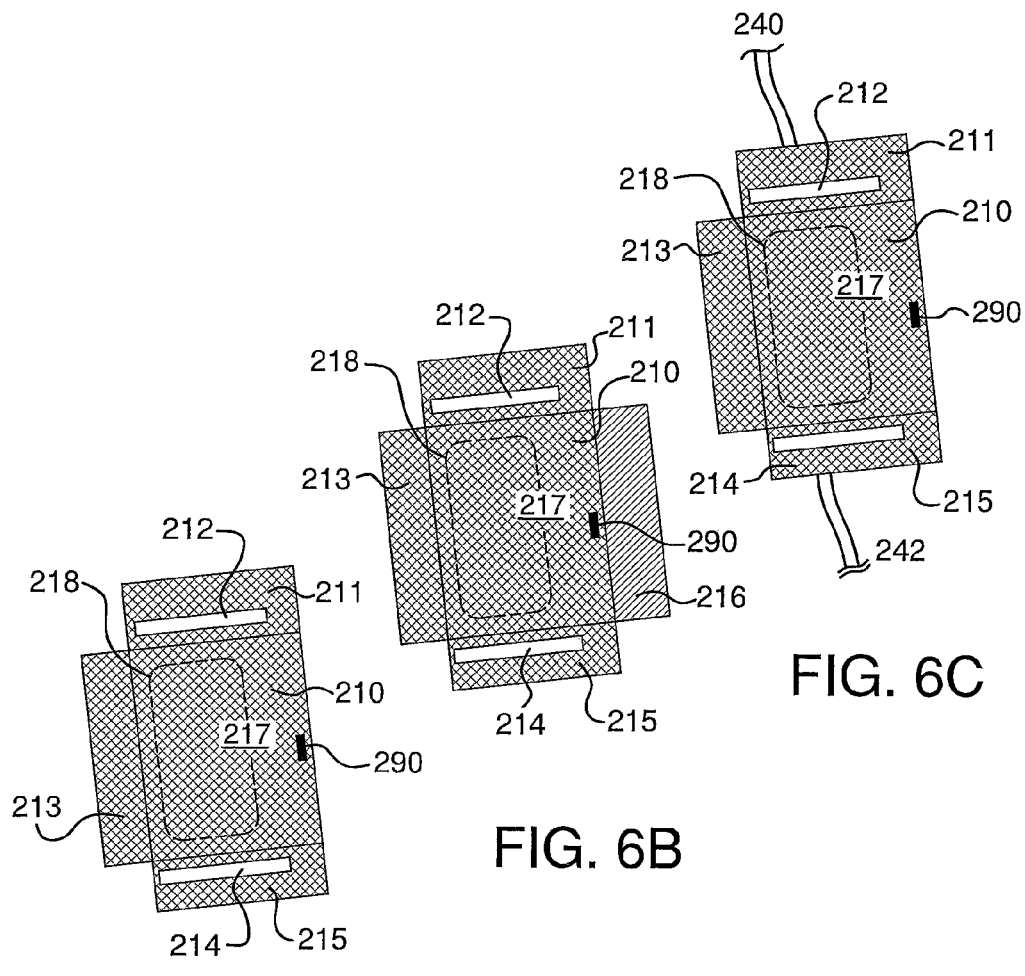
FIGS. 6A-6C each depict a top view of an embodiment of the bucky-side compression devices of the present invention.

FIG. 6A is a top view of a compression device 217 in accordance with the invention that can be positioned over the bucky 4 and imaging area 11, i.e., beneath the breast when the breast is in position on mammography unit (hereinafter referred to as a "bucky-side compression device"). Bucky-side compression device 217 is depicted with optional openings 212, 214, flattened, to show sections 210, 211, 213, and 215 for covering patient-contact surfaces of a cassette holder. In one example, a compression device 217 is at least partly fabricated with a compressible material. Compressible material is preferably low Z elastic matrix material. An identifier 290 is partially radiopaque such that information about the material can be imparted onto a mammogram.

Bucky-side compression device 217 is equipped with one or more x-ray transparent inflatable chambers 218 having at least one manifold (not shown) that is operatively associated with each inflatable chamber, which can introduce compressed gas, for example, into the chamber 218 and/or receive compressed gas to vent it from the chamber 218. A source of fluid, for example, compressed air, enters one or more chambers 218 of the bucky-side compression device 217 through a manifold (not shown). An optional second manifold can be operatively with the chamber 218 for venting or fluid inlet purposes.

In another example, as shown in FIG. 6B, the compression device of FIG. 6A is depicted with optional section 216 which is an extension of the compressible material that can be adapted with methods for retaining the compressible material in place on the cassette holder. Furthermore, there is no limitation on the material used to fabricate section 216. Although x-ray transparent compressible material may be used to facilitate ease of manufacture of the bucky-side compression device, it is understood that oftentimes section 216 need not be x-ray transparent, because x-ray beams do not need to penetrate that area, nor compressible, because a patient typically does not contact that area. Optional section 216 can be integral with the bucky-side compression device 217 or attached separately.

In yet a further example, as shown in FIG. 6C, the bucky-side compression device of FIG. 6A is depicted with optional fasteners 240 and 242 which secure the device by wrapping around the underside of the support member 5. One fastener is shown on each opposite side of the bucky-side compression device, however, it is contemplated that multiple fasteners are suitable for attaching along either side. Furthermore, one fastener can be used which secures to an opposite side of the bucky-side compression device. In another embodiment, the compression device depicted in FIG. 6C can be paddle-mounted. In this embodiment, only section 210 is preferably present, and the attached ends of fasteners 240, 242 can be affixed to section 210 of the device, the loose ends being used to secure the paddle-mounted device to the paddle.

Fasteners can be straps that meet underneath the support member or above the paddle and tie together. In another example, fasteners can engage with each other using hook and loop fasteners. Yet another embodiment includes fasteners that can be one-piece elastic bands which are fixed to opposite sides of the compression device. The fasteners can be fabricated of any material suitable for fastening and unfastening. For ease of manufacture, however, it may be desirable to fabricate the fasteners out of the compressible material of the bucky-side compression device. Fasteners can be integral with the bucky-side compression device or paddle, or may be attached separately.

Figure 7A:
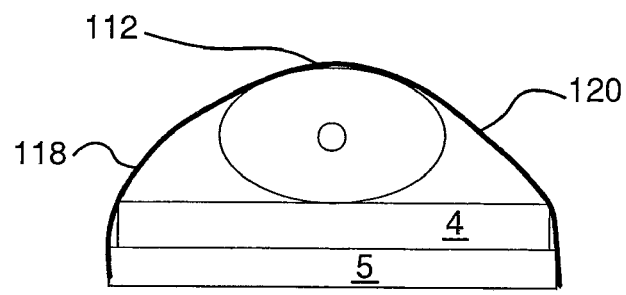
FIGS. 7A-7C provide front views of an embodiment of the tube-side, bucky-side, and paddle-mounted compression devices, respectively, of the present invention.

In FIG. 7A, depicting a side view of an embodiment of the present invention, a compression device is positioned over a patient's breast in contact with the tube-side surface of the breast, referred to as such because this is the surface facing an x-ray tube of the mammography unit. In this embodiment, there are two side flaps 118 and 120 that secure the breast to the bucky 4 and attach to support member 5 (when a film-based bucky is being used). As shown in FIG. 8A, a free end of a first flap 130 can have a first fastener, 132. A second free end 138 can have a second fastener 140. The fasteners are optionally attachable or engagable with each other or individually to the bottom of the support member or bucky. In another example, a flap is secured, either permanently or removable, to a surface of the bucky. Generally, when in position over the breast (and not inflated) as shown in FIG. 7, the one or more inflatable chambers 112 partially conform to the shape of the breast. Compressed air, for example, can be introduced, manually or automatically, to inflate the chamber 112.

Figure 7B:
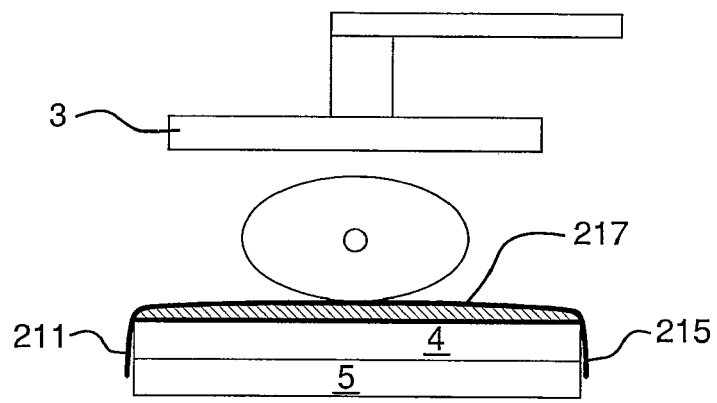
Figure 8A:
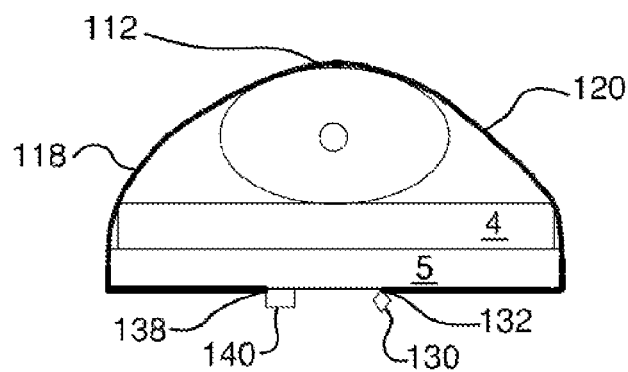
FIGS. 8A-8C provide front views of another embodiment of the tube-side, bucky-side, and paddle-mounted compression devices, respectively, of the present invention.
Figure 8B:
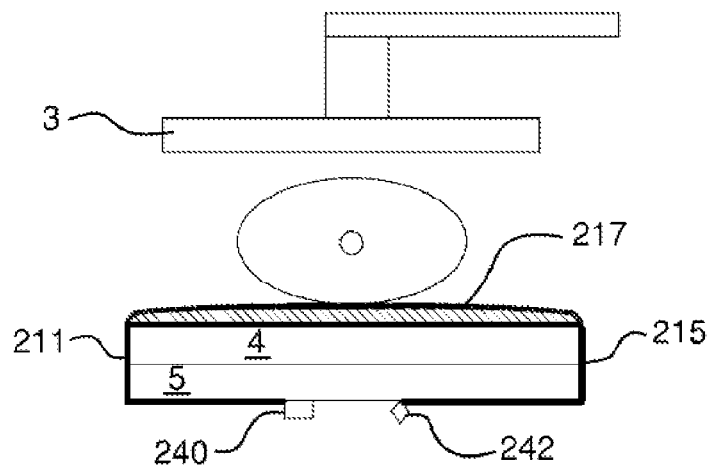

FIG. 7B provides a side view of another embodiment of the present invention in which a bucky-side compression device 217 is positioned between a patient's breast and the bucky 4, in contact with the bucky-side portion of the breast. There may be two side flaps 211 and 215 that secure the breast to the bucky 4, and may attach to support member 5 (when a film-based bucky is being used). As shown in FIG. 8B, a free end of a first flap 211 can have a first fastener, 240. A free end of second flap 215 can have a second fastener 242. The fasteners are optionally attachable or engagable with each other or individually to the bottom of the support member or bucky. Generally, when in position beneath the breast (and not inflated) as shown in FIGS. 7B & 8B, the inflatable chamber (s) 218 (internal—not shown) of the bucky-side compression device 217 partially conforms to the shape of the breast. Compressed air, for example, can be introduced, manually or automatically, to inflate the chamber 218.

Figure 7C:
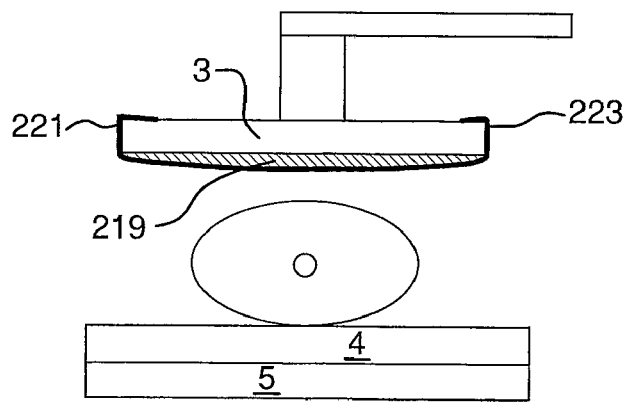
Figure 8C:
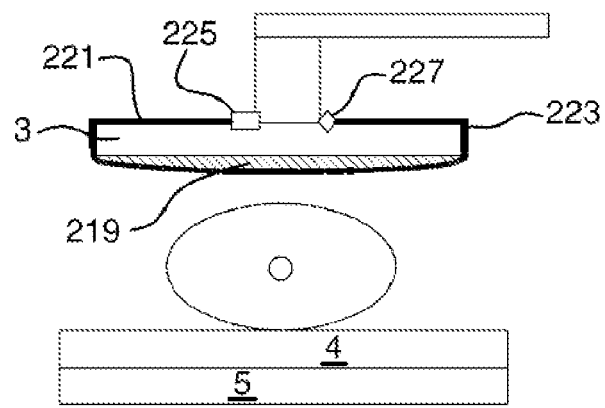

FIG. 7C provides a side view of yet another embodiment of the present invention in which a paddle-mounted compression device 219 is provided. There may be two side flaps 221 and 223 that secure the breast to the paddle 3. As shown in FIG. 8C, a free end of a first flap 221 can have a first fastener, 225. A free end of second flap 223 can have a second fastener 227. The fasteners are optionally attachable or engagable with each other or individually to the bottom of the support member or bucky. Generally, when in position on the underside of the paddle (and not inflated) as shown in FIGS. 7C & 8C, the inflatable chamber(s) (internal—not shown) of the paddle-mounted compression device 219 partially conforms to the shape of the breast. Compressed air, for example, can be introduced, manually or automatically, to inflate the chamber.

Figure 9A:
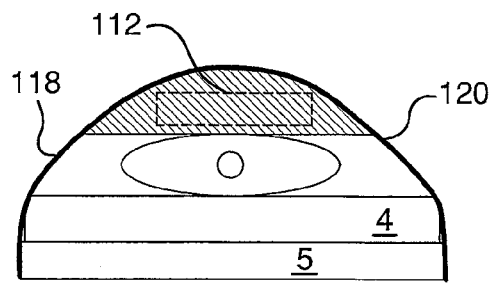
FIGS. 9A-9D depict front views of tube-side, bucky-side, both tube-side and bucky-side, and both bucky-side and paddle-mounted compression devices, respectively, of the present invention.
Figure 9B:
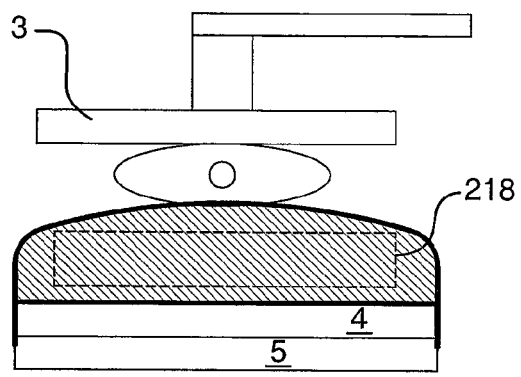
Figure 9C:
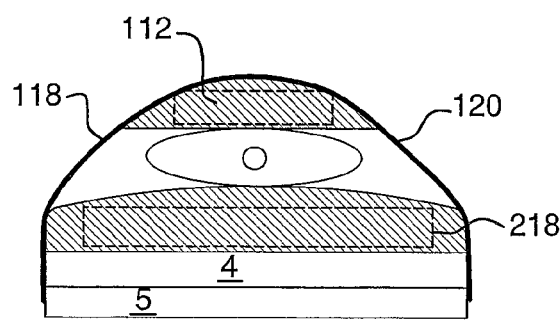
Figure 9D:
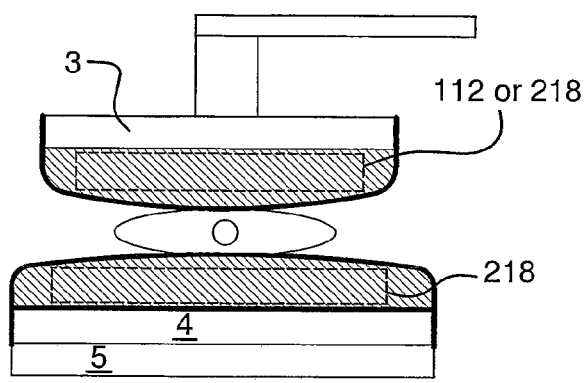

As illustrated in FIG. 9A, when fluid is introduced into a chamber 112 of the tube-side compression device, at least one surface of the chamber expands in the direction of the bucky 4. As the chamber expands, breast motion is limited and the breast is compressed against the bucky 4. Likewise, as depicted in FIG. 9B, when fluid is introduced into a chamber 218 of a bucky-side compression device, at least one surface of the chamber expands in the direction of the compression surface 3 (which may be a paddle or a tube-side compression device according to the present invention), and as the chamber 218 expands, the breast is compressed against the compression surface 3. FIG. 9C provides an embodiment of the current invention in which both a tube-side and a bucky-side compression device are present, and wherein fluid has been introduced into chamber 112 of the tube-side device and into chamber 218 of the bucky-side device. The breast is compressed between the tube-side and bucky-side devices by the expansion of chambers 112 and 218. FIG. 9D provides an embodiment of the current invention in which both a paddle-mounted and a bucky-side compression device are present, and wherein fluid has been introduced into the inflatable chamber (112 or 218) of the paddle-mounted device and into the inflatable chamber 218 of the bucky-side device. The breast is compressed between the paddle-mounted and bucky-side devices by the expansion of the chambers of the respective devices.

Figure 10:
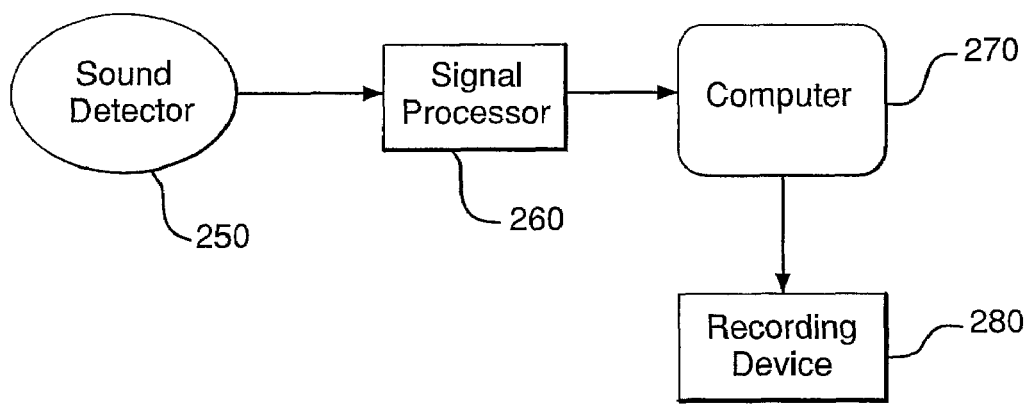
FIG. 10 provides one possible arrangement among components that may be used to detect, store, and process sound information from within a patient's breast.

FIG. 10 depicts one possible arrangement among components that may be used to detect, store, and process sound information from within a patient's breast. A sound detector 250 is preferably placed in fluid communication with a breast, so that sounds may be faithfully transmitted therebetween. For example, the sound detector 250 may be affixed to the outer surface of the breast, or may be contacted with the inflatable chamber of a compression device in accordance with present invention. The sound information received by the detector 250 is transmitted to signal processor 260, which performs a conversion of the acoustical information received by the sound detector 250 into a frequency domain signal that is suitable for transfer by a computer 270. Computer 270 includes software for analyzing the data obtained from the signal processor 260. For example, the analysis software may include an algorithm that incorporates the sound data into a CAD program that uses the sound data and x-ray data to mark sites of interest on a mammogram. A recording device 280 stores the output of the computer software analysis and makes it available for retrieval, for example, by a radiologist or other clinician.

Figure 11A:
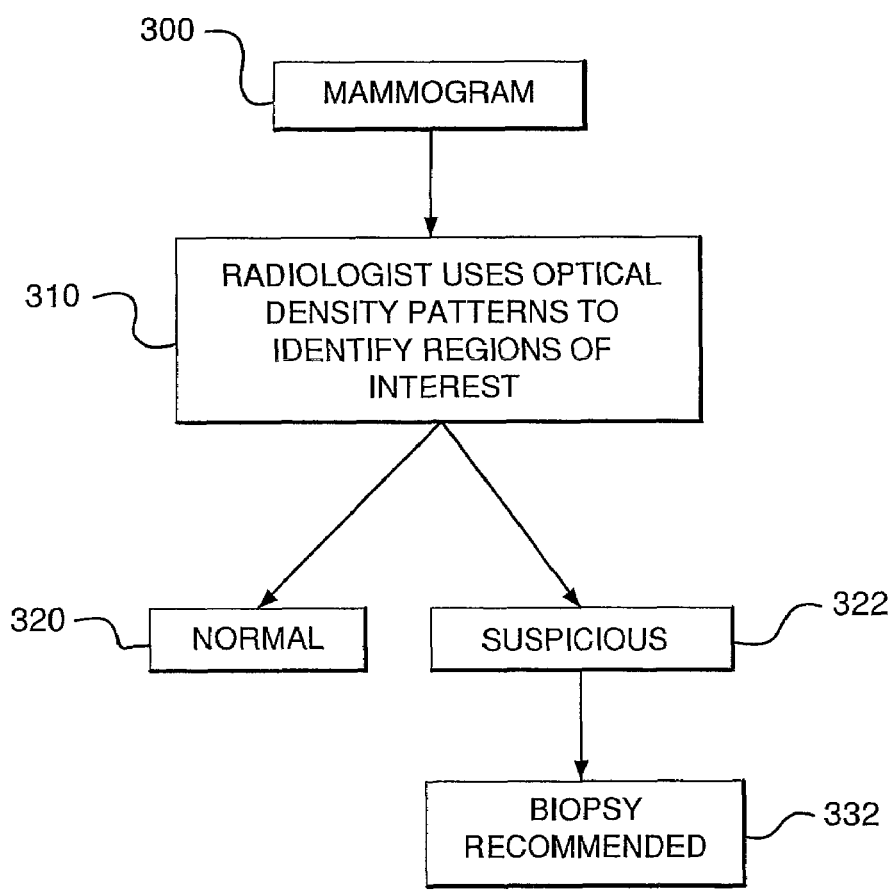
FIGS. 11A & 11B illustrate prior art and inventive mammography procedures, respectively.
Figure 11B:
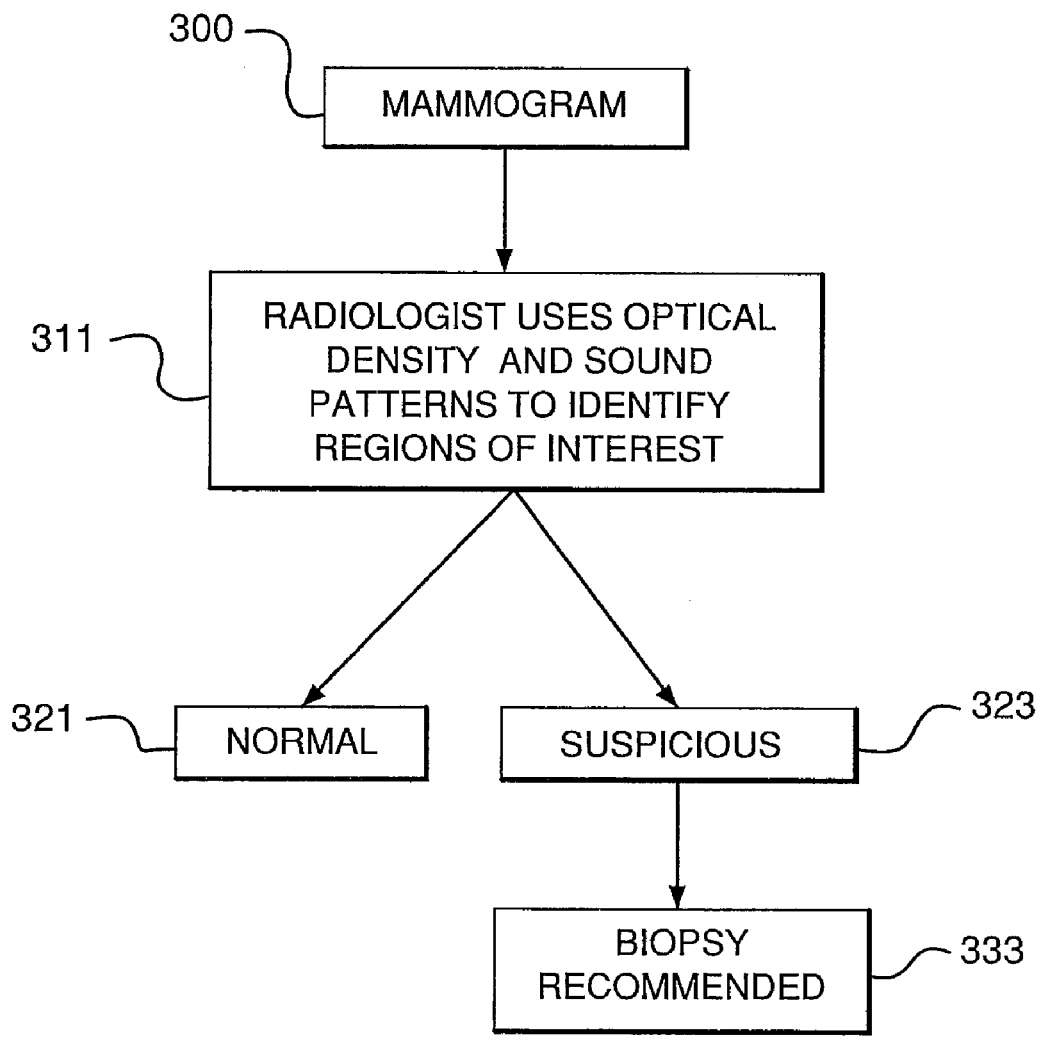

FIGS. 11A & 11B illustrate prior art and inventive mammography procedures, respectively. Referring to FIG. 11A, in accordance with traditional procedures, the patient's breast is positioned on a mammography unit, and a mammogram is conducted 300 to acquire an image of the breast. Next, at step 310, the mammogram image is generated and the attending radiologist will analyze the optical density patterns present on the image in order to identify regions of interest that may indicate the presence of cancerous growth. The radiologist may also conduct an analysis of a CAD-generated image corresponding to the mammogram acquired in step 300. If the radiologist concludes that the visual region of interest represents normal tissue at step 320, no further action is taken. However, if the radiologist believes that the visual region of interest could represent cancerous growth at step 322, a recommendation will be made to conduct a biopsy 332 at the region of interest.

In accordance with one embodiment of the present invention (FIG. 11B), following the acquisition of a mammogram at step 300, the radiologist may refer to both optical density data, and sound pattern data as collected by a sound detector (step 311) in order to identify regions of interest within a patient's breast. Step 311 may additionally comprise comparing sound pattern data obtained from a first of a patient's breasts to the sound data obtained from the patient's contralateral breast. The comparison can yield information relating to the blood flow characteristics of the respective breasts, and can yield a comparison metric that can in turn be applied to the analysis of the mammogram obtained at step 300. The additional data parameter of sound is therefore used to render more precise the step of identifying regions of interest. If the radiologist concludes that the region of interest represents normal tissue at step 321, no further action is taken. However, if the radiologist believes that the visual region of interest could represent cancerous growth at step 323, a recommendation will be made to conduct a biopsy 333 at the region of interest. It is anticipated that the number of unnecessary biopsies that are recommended by the radiologist will become attenuated through the use of the sound data parameter in combination with the optical density patterns present on the mammogram.

Figure 12:
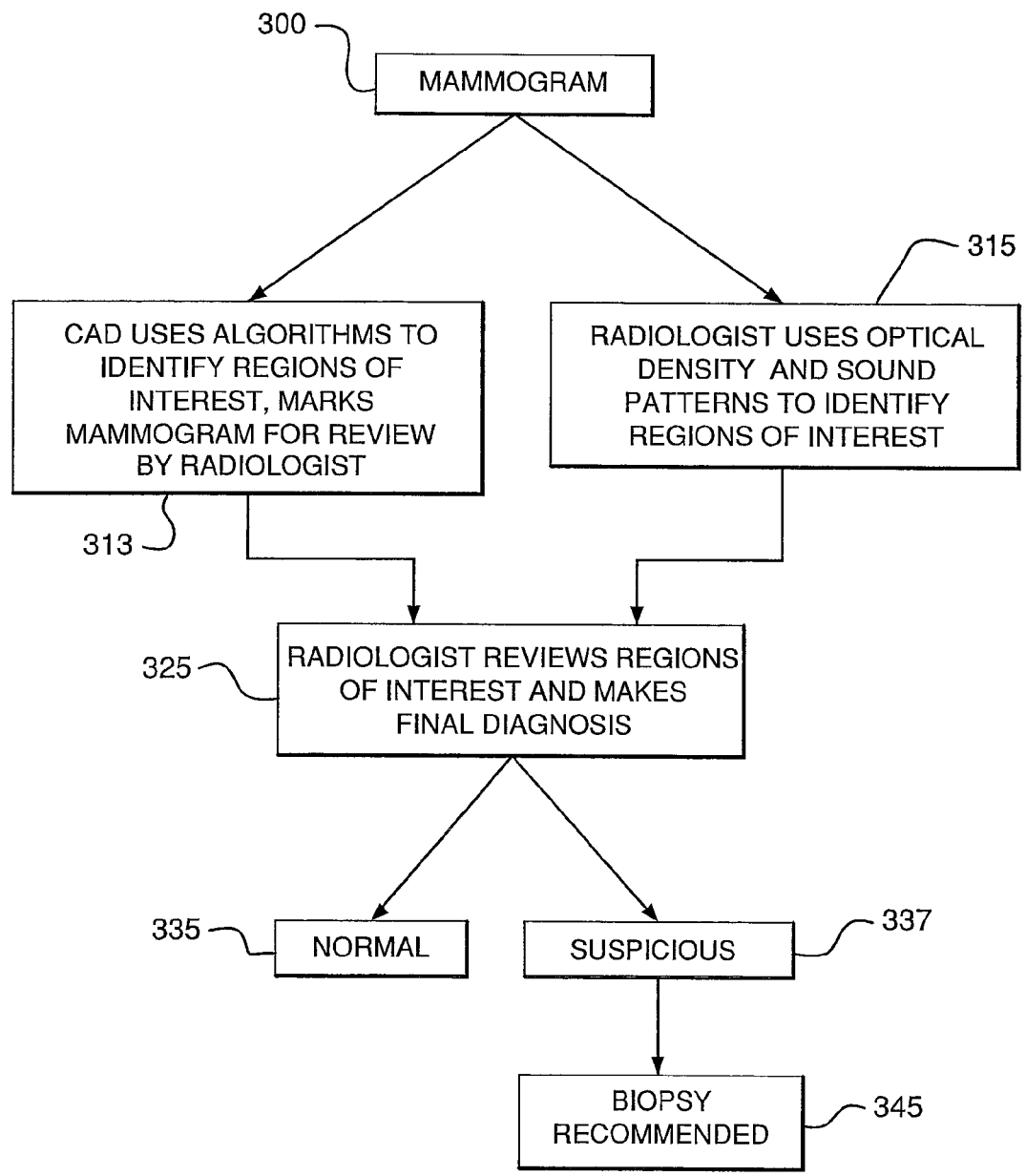
FIG. 12 depicts a mammography procedure in accordance with an embodiment of the present invention.

CAD processes may be used to aid in the interpretation of mammograms, using specific algorithms to flag possible regions of interest for review by a radiologist. In an embodiment of the present invention (FIG. 12), the radiologist may refer to both optical density and sound pattern data as collected by a sound detector (step 315) in order to identify regions of interest within a patient's breast. Step 315 may additionally comprise comparing sound pattern data obtained from a first of a patient's breasts to the sound data obtained from the patient's contralateral breast. The comparison can yield information relating to the blood flow characteristics of the respective breasts, and can yield a comparison metric that can in turn be applied to the analysis of the CAD evaluation obtained at step 313. Additionally, the radiologist may review CAD-generated recommendations 313 as to possible regions of interest within the patient's breast. Based on these sources of data 313, 315, the radiologist may make a diagnosis 325 as to the highlighted anatomical regions, which may be that the regions of interest represent normal tissue 335, or that they may be indicative of cancerous growth 337. In the latter instance, the radiologist may recommend a biopsy 345 on one or more of the regions of interest.

Figure 13:
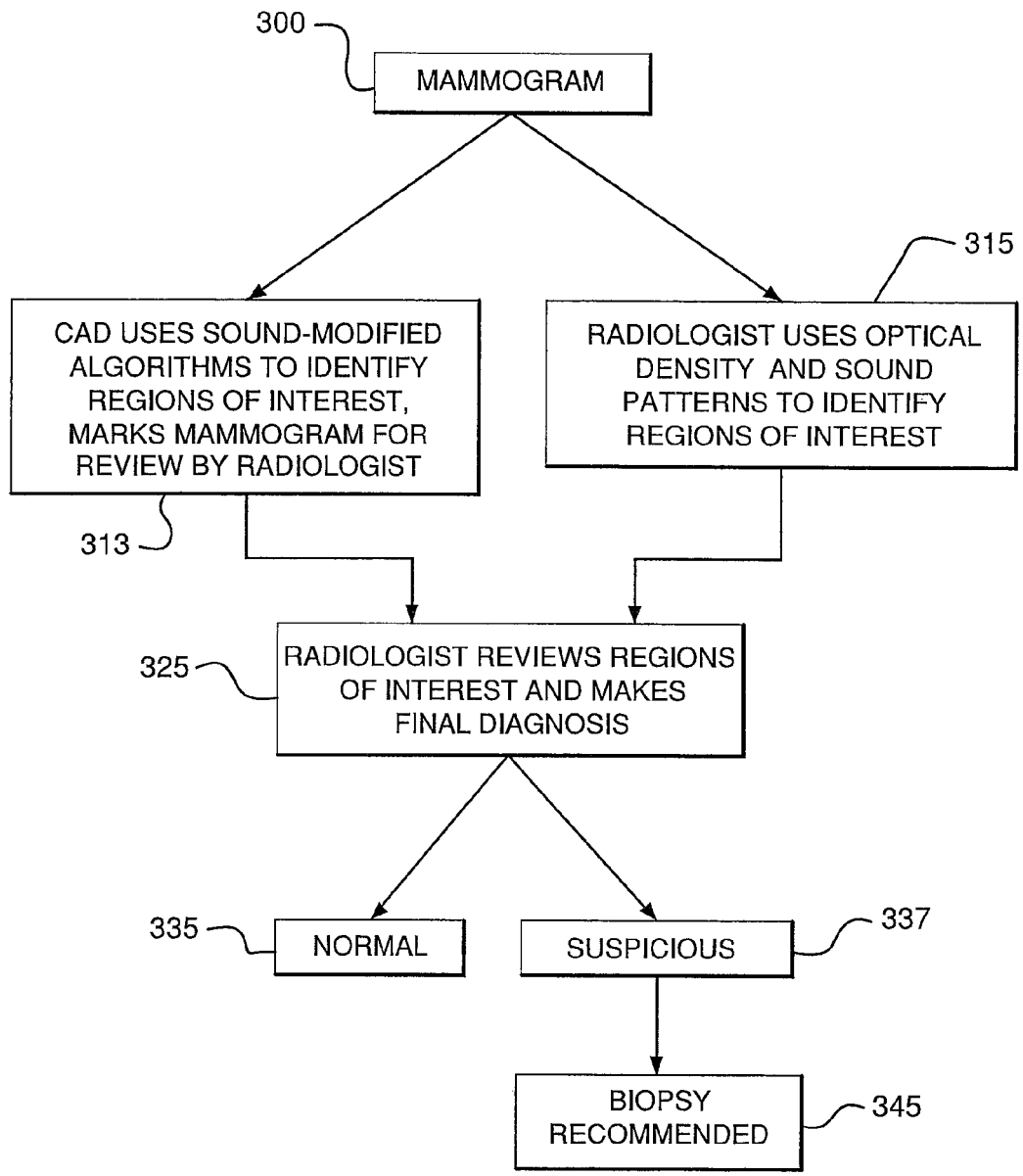
FIG. 13 depicts a mammography procedure in accordance with another embodiment of the present invention.

In accordance with the present invention, the CAD algorithms themselves may be tailored to process sound data, including a comparison metric that results from the comparison of sound data from a first and contralateral breast, respectively, as acquired at some time before, during, or after a mammogram 300 is acquired. Thus, as illustrated in FIG. 13, in addition to processing the data parameter of optical densities, the CAD algorithm may be structured to process data acquired through sound detection and mark a mammogram to identify potential regions of interest (317). The radiologist may also perform a visual analysis of the mammogram 319, and review all potential regions of interest in order to make a diagnosis 327. The regions of interest may be deemed normal tissue 338, or may be considered to be suggestive of cancerous growth 339. In the latter instance, the radiologist may recommend a biopsy 347 on one or more of the regions of interest.

While the invention has been described and illustrated with reference to specific embodiments, those skilled in the art will recognize that modifications and variations may be made without departing from the principles of the invention as described herein and set forth in the following claims.

What is claimed:

1. A method comprising:
   (a) securing a first compression device comprising an x-ray transparent inflatable chamber over a tube-side surface of a first breast of a patient positioned on an imaging area of a bucky on a mammography unit;
   (b) at least partially filling the inflatable chamber of the first compression device with a fluid, thereby compressing the breast between the inflatable chamber and the imaging area and at least partially occluding blood flow to the breast;
   (c) transmitting x-rays through the breast;
   (d) releasing at least a portion of the fluid from the inflatable chamber, wherein the release of the fluid from the chamber controls the resumption of blood flow to the breast;
   (e) detecting sounds generated by the resumption of blood flow to the breast; and,
   (f) repeating each of said steps (a)-(e) with respect to said patient's contralateral breast.

2. The method according to claim 1 further comprising detecting sounds within said first breast and said contralateral breast when said breasts are not compressed.

3. The method according to claim 2 comprising detecting sounds within said first breast and said contralateral breast prior to at least partially filling the inflatable chamber of the first compression device.

4. The method according to claim 2 comprising detecting sounds within said first breast and said contralateral breast following said releasing of the fluid from the inflatable chamber and after blood flow to the respective breast has been substantially completely restored.

5. The method according to claim 1 further comprising securing a second compression device comprising an x-ray transparent inflatable chamber over the imaging area of the bucky, and at least partially filling the inflatable chamber of the second compression device with a fluid, thereby compressing said first breast and said contralateral breast, respectively, between the inflatable chamber of the second compression device and the first compression device.

6. The method according to claim 1 further comprising administering to said patient an x-ray-opaque contrast agent prior to releasing at least a portion of the fluid from the inflatable chamber.

7. The method according to claim 6 further comprising transmitting x-rays through said first breast and said contralateral breast after releasing at least a portion of the fluid from the inflatable chamber.

8. The method according to claim 1 further comprising comparing said detected sounds from said first breast with said detected sounds from said contralateral breast.

9. The method according to claim 8 wherein said comparison provides a comparison metric, and further comprising using said metric during the analysis of at least one of a computer-assisted detection process, a mammogram, or a database of mammography images.

10. A method comprising:
    (a) securing a first compression device comprising an x-ray transparent inflatable chamber over an imaging area of a bucky of a mammography unit, so that when a first breast of a patient is positioned upon the imaging area, the breast is interposed between the first compression device and a compression surface positioned above a tube-side surface of the breast;

(b) at least partially filling the inflatable chamber of the first compression device with a fluid, thereby compressing the breast between the inflatable chamber and the compression surface and at least partially occluding blood flow to the breast;

(c) transmitting x-rays through the breast;

(d) releasing at least a portion of the fluid from the inflatable chamber, wherein the release of the fluid from the chamber controls the resumption of blood flow to the breast;

(e) detecting sounds generated by the resumption of blood flow to the breast; and (f) repeating each of said steps (a)-(e) with respect to said patient's contralateral breast.

11. The method according to claim 10 wherein said compression surface is a paddle.

12. The method according to claim 11 further comprising securing a second compression device comprising an x-ray transparent inflatable chamber to said paddle, and at least partially filling the inflatable chamber of the second compression device with a fluid, thereby compressing said first breast and said contralateral breast, respectively, between the inflatable chamber of the second compression device and the first compression device.

13. The method according to claim 10 further comprising detecting sounds within said first breast and said contralateral breast when said breasts are not compressed.

14. The method according to claim 10 further comprising detecting sounds within said first breast and said contralateral breast prior to at least partially filling the inflatable chamber of the first compression device.

15. The method according to claim 10 further comprising detecting sounds within said first breast and said contralateral breast following said releasing of the fluid from the inflatable chamber and after blood flow to the respective breast has been substantially completely restored.

16. The method according to claim 10 further comprising comparing said detected sounds from said first breast with said detected sounds from said contralateral breast.

17. The method according to claim 16 wherein said comparison provides a comparison metric, and further comprising using said metric during the analysis of at least one of a computer-assisted detection process, a mammogram, or a database of mammography images.

18. A method comprising:

(a) securing a first compression device comprising an x-ray transparent inflatable chamber to a compression paddle of a mammography unit having a bucky with an imaging area;

(b) at least partially filling the inflatable chamber of the first compression device with a fluid, thereby compressing a first breast of a patient that is positioned on the bucky between the inflatable chamber and the imaging area, and at least partially occluding blood flow to the breast;

(c) transmitting x-rays through the breast;

(d) releasing at least a portion of the fluid from the inflatable chamber, wherein the release of the fluid from the chamber controls the resumption of blood flow to the breast;

(e) detecting sounds generated by the resumption of blood flow to the breast; and, (f) repeating each of steps (a)-(e) with respect to said patient's contralateral breast.

19. The method according to claim 18 further comprising securing a second compression device comprising an x-ray transparent inflatable chamber over the imaging area of the bucky, and at least partially filling the inflatable chamber of the second compression device with a fluid, thereby compressing said first breast and said contralateral breast, respectively, between the inflatable chamber of the second compression device and the first compression device.

20. The method according to claim 18 further comprising comparing said detected sounds from said first breast with said detected sounds from said contralateral breast.

21. The method according to claim 20 wherein said comparison provides a comparison metric, and farther comprising using said metric during the analysis of at least one of a computer-assisted detection process, a mammogram, or a database of mammography images.

22. A method comprising interpreting a mammogram of a patient's first breast using a comparison of data derived from the detection of Korotkoff sounds within said first breast and data derived from the detection of Korotkoff sounds within said patient's contralateral breast.

23. The method according to claim 22 wherein said data is used to designate one or more regions of interest on said mammogram.

24. The method according to claim 22 wherein said data is used during a computer-assisted detection process.

25. A method comprising:

(a) compressing a first breast of a patient, whereby the resulting compression occludes at least some blood flow to the breast;

(b) at least partially relieving such compression, such that blood flow to the breast is at least partially restored;

(c) detecting Korotkoff sounds within the breast; and, (d) repeating each of steps (a)-(c) with respect to said patient's contralateral breast.

26. The method according to claim 25 further comprising comparing said detected Korotkoff sounds from said first breast with said detected Korotkoff sounds from said contralateral breast.

27. The method according to claim 26 wherein said comparison provides a comparison metric, and further comprising using said metric during the analysis of at least one of a computer-assisted detection process, a mammogram, or a database of mammography images.

28. The method according to claim 25 comprising using data derived from the detection of Korotkoff sounds within said first breast and said contralateral breast to designate regions of interest on a mammogram.

29. The method according to claim 28 wherein said data is used during a computer-assisted detection process.

30. The method according to claim 25 further comprising transmitting x-rays through said first breast to obtain a first mammogram, and transmitting x-rays through said contralateral breast to obtain a second mammogram.

* * * * *